United States Patent [19]

Paulik et al.

[11] Patent Number: 4,810,821

[45] Date of Patent: Mar. 7, 1989

[54] PREPARATION OF ALKYLIDENE DIESTERS

[75] Inventors: Frank E. Paulik; Robert G. Schultz, both of Creve Coeur, Mo.

[73] Assignee: Monsanto Company, St. Louis, Mo.

[21] Appl. No.: 739,723

[22] Filed: May 31, 1985

Related U.S. Application Data

[63] Continuation of Ser. No. 584,205, Feb. 27, 1984, abandoned, which is a continuation-in-part of Ser. No. 309,949, Oct. 9, 1981, abandoned, which is a continuation-in-part of Ser. No. 591,919, Jun. 30, 1975, and Ser. No. 111,411, Jan. 11, 1980, abandoned, which is a continuation-in-part of Ser. No. 591,919.

[51] Int. Cl.$^4$ .................. C07C 67/36; C07C 67/37; C07C 69/16
[52] U.S. Cl. .................. 560/232; 203/88; 260/546; 260/549; 562/517; 585/733
[58] Field of Search .................. 560/232

[56] References Cited

FOREIGN PATENT DOCUMENTS 1538782 1/1979 United Kingdom ............ 560/232

OTHER PUBLICATIONS

*Chemical Abstracts*, 85, 17687c (1976).

*Primary Examiner*—Vivian Garner
*Attorney, Agent, or Firm*—Wendell W. Brooks; Richard H. Shear; Arnold H. Cole

[57] ABSTRACT

Alkylidene diesters such as ethylidene diacetate are selectively produced in high yields by reacting an ether and/or an ester under substantially anhydrous conditions with carbon monoxide and hydrogen in contact with a catalyst system comprising a rhodium compound, a halogen component, a palladium cocatalyst and a promoter component which is an agent for liberation of carboxylic acid anions. The process is carried out in the liquid phase in a solvent comprising a carboxylic acid at a temperature in the range of 150° to 190° C. and at a carbon monoxide partial pressure in the range from about 1.0 to 1100 kg/cm$^2$ and a carbon monoxide/hydrogen mole ratio of 6:1 to 1:2 for the ester reaction and 10:1 to 1:2 for the ether reaction. When ethylidene diacetate is the product, it can then be decomposed to produce vinyl acetate and acetic acid by well-known techniques. Since one mole of acetic acid is also produced in the synthesis of the diacetate, the invention makes possible an overall process for the production of vinyl acetate which produces acetic acid rather than consumes it.

20 Claims, No Drawings

PREPARATION OF ALKYLIDENE DIESTERS

CROSS-REFERENCE TO RELATED APPLICATIONS

This is a continuation of application Ser. No. 584,205, filed Feb. 27, 1984, now abandoned, which is a continuation-in-part of copending application Ser. No. 309,949, filed Oct. 9, 1981, now abandoned, which is a continuation-in-part of copending application Ser. No. 591,919, filed June 30, 1975, and application Ser. No. 111,411, filed Jan. 11, 1980, now abandoned, which is a continuation-in-part of application Ser. No. 591,919.

BACKGROUND OF THE INVENTION

The present invention relates to a new process for the production of alkylidene diesters at high selectivities and yields and, more particularly, to the high yield production of ethylidene diacetate which is readily convertible to vinyl acetate.

It is known to produce vinyl esters of the type having the general formula

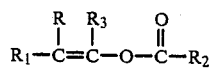

in which R, $R_1$ and $R_3$ may be either hydrogen or alkyl and $R_2$ is an alkyl group. The oldest commercial process for producing vinyl acetate, the most important of these esters, for example, involves the reaction of acetaldehyde and acetic anhydride to produce ethylidene diacetate which is then catalytically decomposed to give vinyl acetate. Because of the high cost of producing the acetic anhydride starting material, however, most vinyl acetate now made commercially is produced by processes which start with either ethylene or acetylene and with acetic acid. A method is described in copending application Serial No. 591,919, whereby the ethylidene diacetate can be produced directly from more readily available raw materials than those of the prior art. The diester can then be catalytically cracked to the vinyl ester produced, two moles of acetic acid are simultaneously produced, one in the synthesis of the diester and one in its conversion, and no acetic acid is consumed in the process. This process, while quite satisfactory in most respects, exhibits coproduction of acetic anhydride with ethylidene diacetate which may be desirable in some situations. The present invention provides a process which gives improved selectivity and yield of diesters, minimizing the coproduction of acetic anhydride.

SUMMARY OF THE INVENTION

According to the present invention, a highly selective process for production of alkylidene diesters from ether or ester raw materials is provided. The novel selective catalyst system employs a palladium and rhodium-containing cocatalyst system, a halogen component which is bromine, iodine, a bromide, or an iodide, and a component which is an agent for liberation of carboxylic acid anions. Another feature of the present invention is the inclusion of minor amounts of a specific acid as a reactant as described below.

The critical distinction between the catalyst system of the invention and the known processes is the presence of the palladium cocatalyst. Other important distinctions are (a) the inclusion of a component for liberation of carboxylic acid anions, and (b) a specific solvent system containing at least 9% of the carboxylic acid whose ester is to be produced. It is these critical and distinguishing features, and particularly the palladium cocatalyst component, which enable the carbonylation of the ether or ester feedstock at particularly high selectivities to the alkylidene diester while maintaining high levels of conversion of the feedstock. Quite surprisingly, it has been found that other metals from Group 8 of the Periodic Table of the Elements (as published in *CRC Handbook of Chemistry and Physics*, 59th ed. Weast, Ed., CRC Press, Inc., West Palm Beach, Fla., 1978, Inside Front Cover) do not have the beneficial cocatalyst effect exhibited by palladium in this carbonylation reaction, although some of the other Group 8 metals have been known in the art to be quite similar to palladium in their catalytic action in other reaction systems.

Contacting of the ether or ester raw material with the catalyst and a mixture of carbon monoxide and hydrogen is carried out under substantially anhydrous conditions at a temperature in the range of from about 150° C. to about 190° C. and at a carbon monoxide partial pressure in the range from about 1.0 to about 1100 kg/cm². The alkylidene diester, if desired, can then be decomposed to the corresponding vinyl ester by methods well known in the art.

DESCRIPTION OF THE PREFERRED EMBODIMENTS

To achieve high conversions and selectivities to the alkylidene diester, a soluble palladium compound is an essential part of the present invention as cocatalyst since the addition of such compounds to the system has a significant effect on the diester/acid anhydride ratio. Suitable compounds for use as cocatalyst include but are not limited to palladium chloride, palladium acetate, palladium iodide, palladium acetylacetonate and the like. The amount of the palladium compound employed may vary from about 0.1 to about 10 moles per mole of the rhodium compound of the catalyst system and preferably is from about 0.25 to about 4 moles per mole of the rhodium compound employed.

In addition to the palladium cocatalyst which is an essential component of the present invention, the catalyst system includes a rhodium compound and a halogen component in which the halogen component is either bromine, iodine, a bromide compound or an iodide compound. Generally, the rhodium compound of the catalyst system of the present invention is believed to be present in the form of a coordination compound of rhodium with at least one of the ligands of such coordination compound provided by halogen ligands, carbon monoxide ligands and the like. Generally, it is preferred that the catalyst system contain as a promoting component, an excess of halogen over that present as ligands in the rhodium coordination compound. The terms "coordination compound" and "coordination complex" used throughout this specification mean a compound or complex formed by combination of one or more electronically rich molecules or atoms capable of independent existence with one or more electronically poor molecules or atoms, each of which may also be capable of independent existence.

The essential rhodium compound and the halogen component of the catalyst system of the present invention may be provided by introducing into the reaction zone a coordination compound of rhodium containing halogen ligands or they may be provided by introducing into the reaction zone separately a rhodium compound and a halogen compound. The rhodium compound can be provided by any material that will produce rhodium ions. Among the materials which may be charged to the reaction zone to provide the rhodium compound of the catalyst system of the present invention are rhodium metal, rhodium salts, rhodium oxides, rhodium carbonyl compounds, organorhodium compounds, coordination compounds of rhodium and the like. Specific examples of materials capable of providing the rhodium constituent of the catalyst system of the present invention may be taken from the following nonlimiting partial list of suitable examples.

| | |
|---|---|
| $RhCl_3$ | $[(n-C_4H_9)_4N][Rh(CO)_2X_2]$ where $X = Cl^-, Br^-, I^-$ |
| $RhBr_3$ | $[(n-C_4H_9)_4As]_2[Rh_2(CO)_2Y_4]$ where $Y = Br^-, I^-$ |
| $RhI_3$ | $[(n-C_4H_9)_4P][Rh(CO)I_4]$ |
| $RhCl_3.3H_2O$ | $Rh[(C_6H_5)_3P]_2(CO)Br$ |
| $RhBr_3.3H_2O$ | $Rh[(n-C_4H_9)_3P]_2(CO)Br$ |
| $Rh_2(CO)_4Cl_2$ | $Rh[(n-C_4H_9)_3P]_2(CO)I$ |
| $Rh_2(CO)_4Br_2$ | $RhBr[(C_6H_5)_3P]_3$ |
| $Rh_2(CO)_4I_2$ | $RhI[(C_6H_5)_3P]_3$ |
| $[Rh(CO)I_4]Na$ | $[Rh(CO)Br_4]Na$ |
| $Rh_2(CO)_8$ | $RhCl[(C_6H_5)_3P]_3$ |
| $Rh[(C_6H_5)_3P]_2(CO)I$ | $RhCl[(C_6H_5)_3P]_3H_2$ |
| $Rh[(C_6H_5)_3P]_2(CO)Cl$ | $[(C_6H_5)P]_3Rh(CO)H$ |
| Rh metal | $Rh_2O_3$ |
| $Rh(NO_3)_3$ | $Li[Rh(CO_2I_2]$ |
| $RhCl[(C_6H_5)_3P]_2(CH_3I)_2$ | $[Rh(C_2H_4)_2Cl]_2$ |
| $Rh(SnCl_3)[(C_6H_5)_3P]_3$ | $K_4Rh_2Cl_2(SnCl_3)_4$ |
| $RhCl(CO)[(C_6H_5)_3As]_2$ | $K_4Rh_2Br_2(SnBr_3)_4$ |
| $RhI(CO)[(C_6H_5)_3Sb]_2$ | $K_4Rh_2I_2(SnI_3)_4$ |
| $Na[Rh(CO,_2I_2]$ | $[Rh(CO)_2I_2]K$ |

With those materials listed above as capable of providing the rhodium component which do not contain a halogen component from the group consisting of bromine and iodine, it will be necessary to introduce into the reaction zone such a halogen component. For example, if the rhodium component introduced is rhodium metal or $Rh_2O_3$, it will be necessary to also introduce a halogen component such as methyl iodide, hydrogen iodide, iodine and the like.

Rhodium precursor materials that can be utilized to produce the rhodium compounds useful in our invention are almost limitless. The only requirement is that the rhodium precursor material is capable of producing rhodium ions. The rhodium ions can, of course, be generated from the rhodium precursor material in situ in the reactor utilized in our process.

As noted above, while the halogen component of the catalyst system may be in combined form with the rhodium, as for instance, as one or more ligands in a coordination compound of rhodium, it generally is preferred to have an excess of halogen present in the catalyst system as a promoting component. By excess is meant an amount of halogen greater than two atoms of halogen per atom of rhodium in the catalyst system. This promoting component of the catalyst system consists of a halogen and/or halogen compound such as hydrogen halide, alkyl halide, aryl halide, metal halide, ammonium halide, phosphonium halide, arsonium halide, stibonium halide, and the like. The halogen of the promoting component may be the same or different from that already present as ligands in the coordination compound of rhodium. Iodine and iodide compounds are the preferred halogen components used in our invention. While the bromine or iodine components used in our invention may be in combined form with the rhodium, as for instance, one or more ligands in a complex or coordination compound of the rhodium, it is generally preferred to charge the iodine or bromine component to the catalyst preparation zone or the reactor separately. The bromine or iodine component utilized in the present invention can be provided by many different iodine or bromine precursor materials. Suitable precursor materials include bromine, iodine, any bromide compound or any iodide compound. Accordingly, suitable halogen providing or promoting components may be selected from the following nonlimiting list of halogen and/or halogen-containing compounds.

| | | |
|---|---|---|
| RX | where R = any alkyl or aryl group where X = Br or I | e.g., $CH_3I$, $C_6H_5Br$, $CH_3CH_2I$, etc. |
| $X_2$ or $X_3$ | where X = Br or I | e.g., $Br_2$, $I_2$, $I_3$, etc. |
| HX | where X = Br or I | e.g., HBr, HI |
| $\overset{O}{\underset{\|}{RCX}}$ | where R = any alkyl or aryl group and X = Br or I | $\overset{O}{\underset{\|}{e.g., CH_3Cl, etc.}}$ |
| $R_4MX$, $R_4MX_3$, or $R_3MX_2$ | where R = any alkyl or aryl group M = N, P, As, or Sb X = BR or I | e.g., $(C_4H_9)_4NI$ $(C_6H_5)_3PI_2$ and/or combinations of R, M, and X |

Other nonlimiting examples of such compounds of bromine and iodine include ethyl iodide, ethyl bromide, benzyl iodide, benzyl bromide, sodium iodide, sodium bromide, potassium iodide, potassium bromide, lithium iodide, lithium bromide, barium iodide, magnesium iodide, calcium iodide, 1-decyl iodide, 1-decyl bromide, and the like.

Although any amount of the promoting halogen component of the catalyst system of the present invention may be employed, the amount employed is such as to produce a ratio of atoms of halogen to atoms of rhodium in the catalyst system of from above 2:1 to 50,000:1 and higher. However, the preferred ratio is 5:1 to 5,000:1 and higher. A more preferred ratio of halogen atoms to rhodium atoms is 10:1 to 2500:1.

The active palladium and rhodium-containing catalyst system is preferably employed in the form of a catalyst solution. The solution can also include liquid reactants, products and mixtures thereof which function as solvent or reaction media. The catalyst solutions essentially comprised of (1) the reactant feed component-product diester medium, (2) a rhodium compound, (3) a palladium cocatalyst, (4) a halogen component generally in excess of the rhodium as hereinbefore set forth, and (5) promoter means for liberation of anions of the carboxylic acid of which the ester is to be produced may be further modified by the addition of a high-boiling inert solvent as a further component. Such an inert solvent should have a physical property sufficiently different from that of the product diester to permit easy separation. One convenient physical property is boiling point. A boiling point difference of 25° C. or more is preferred. Inert solvents within the present category include paraffin and cycloparaffin hydrocarbons of from 10 to 30 carbon atoms, aromatic hydrocarbons of from 10 to 40 carbon atoms, tertiary amines of 6 to 20 carbon atoms, and esters of the aforesaid acids, heterocyclic aromatic compounds of 5 to 20 carbon atoms, as well as the chlorine, bromine and iodine-containing derivatives of all of the above said solvents. The following list exemplifies such solvents: dodecane, hexadecane, Tetralin, octanoic acid, benzoic acid, Decalin, N-methylpyrrolidone, and the like. An especially suitable solvent is 1-methylnaphthalene since it provides for catalyst recycle with a minimum loss in catalyst activity.

In accordance with the present invention, however, it is important that the solvent system employed contain at least about 9% of the carboxylic acid of which the diester is to be produced. For example, if ethylidene diacetate is the desired diester product, at least 9% acetic acid is employed in the solvent system. Similarly, if ethylidene dipropionate is desired as the product, propionic acid should be present in a concentration of at least 9%. It is noted, however, that, everything else being equal, the presence of higher concentrations of the carboxylic acid in the solvent system, such as about 45% to about 65%, or higher, are even more beneficial to the overall efficiency of the process of the present invention.

The reaction rate is dependent upon catalyst concentration and temperature. Concentrations of the rhodium-containing component of the catalyst system in the liquid phase between $10^{-6}$ mole/liter and $10^{-1}$ mole/liter are normally employed with the preferred range being $10^{-4}$ mole/liter to $10^{-2}$ mole/liter. Higher concentrations may, however, be used if desired.

In the reaction system of this invention, it has been found that in addition to the above-mentioned rhodium catalyst, halogen promoter component, palladium cocatalyst and carboxylic acid-containing solvent, an agent capable of generating carboxylic acid anions, such as acetate, is necessary if high selectivity to the corresponding diester, such as ethylidene diacetate (EDA), is to be achieved at high conversions of charge stock (ether or ester). As used herein, the terms "agent capable of generating carboxylic acid anions" and "means for generating carboxylic acid anions" are interchangeable and are intended to include such substances as so-called "Lewis bases" having a free electron pair (i.e., proton acceptors) as well as carboxylate salts which are soluble in the charge stock-solvent catalyst system. Exemplary of such substances are tertiary phosphines, tertiary amines, tertiary stibines and tertiary arsines, alkali metal salts of the carboxylic acid of which the diester is the desired product, and mixtures of such substances. Nonlimiting examples of these compounds include triphenylphosphine, tri-n-butylphosphine, tri-n-butylamine, pyridine, quinoline, tri-n-butylstibine, tri-n-butylarsine, lithium acetate, and the like. The molar ratio of such substances to the rhodium component present may be from 1000:1 to 1:1, preferably from about 20:1 to about 2:1.

Suitable feedstocks that can be utilized in this invention to produce alkylidene diesters are compounds which contain an ether group (—C—O—C—) or an ester group

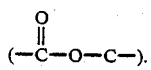

Generally, these suitable feed materials can be represented by the structural formulas

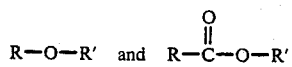

wherein R and R' are saturated aliphatic hydrocarbon groups containing from 1 to 5 carbon atoms each. Mixtures of such ethers and esters can also be used as feed materials. Nonlimiting examples of suitable ether reactant materials that can be utilized in the process of the invention include dimethyl ether, diethyl ether, methyl ethyl ether, diisobutyl ether, ethyl propyl ether, amyl ether, and the like. Nonlimiting examples of suitable ester reactants utilized in the invention are methyl acetate, ethyl acetate, methyl propionate, ethyl propionate, butyl acetate, methyl butyrate, and the like.

The carbonylation reaction of the present invention is carried out by contacting the feedstock in the liquid phase with gaseous carbon monoxide and hydrogen in a liquid reaction medium comprising a carboxylic acid and which contains the catalyst system such as, e.g., $RhCl_3$, a halogen-containing promoting component such as methyl iodide, a palladium cocatalyst such as $PdCl_2$, and an agent for liberating carboxylic acid anions. If the amount of the carboxylic acid is less than about 9%, additional acid will have to be added as a feedstock. The contacting is carried out under the aforementioned suitable conditions of temperature and pressure. The temperature will be in the range of 150° to 190° C. Especially preferred temperatures lie in the range from 160° to 175° C.

Partial pressures of the carbon monoxide in the carbon monoxide-hydrogen mixture of the order of 1.0 kg/cm$^2$ to 1100 kg/cm$^2$ may be employed; however, the partial pressure of the mixture preferred is from 1.5 to 255 kg/cm$^2$ whereas an even more preferred range is from about 35 to 55 kg/cm$^2$. Higher pressures may be used if desired under proper conditions. However, such pressures are rarely used because high reaction rates with good product yields can be obtained by operating at the lower pressures without danger of catalyst decomposition thus providing important economic advantages over prior art methods for producing the alkylidene diesters. As employed herein, the term pressure is expressed as gauge pressure units (kg/cm$^2$-G) as opposed to absolute pressure units (kg/cm$^2$-A).

A typical carbonylation reaction selective to the diester requires at least one mole of carbon monoxide per mole of ester feed. When an ether is employed as feed material, the stoichiometric mole ratios of 2 moles of carbon monoxide per mole of ether is required. Excess of carbon monoxide over the aforesaid stoichiometric amounts, however, may be present. Carbon monoxide streams containing inert impurities such as carbon dioxide, methane, nitrogen, paraffinic hydrocarbons having from 1 to 4 carbon atoms may be employed, if desired, from an available gas plant stream; however, in such cases, total reactor pressure will have to be increased to maintain a desired carbon monoxide partial pressure. Carbon monoxide concentration in the feed gas mixture may range from 1 to 100% but preferably over 10% by volume of carbon monoxide should be present.

A key variable to achieve high diester levels is the quantity of hydrogen present. The stoichiometric ratio suggested by the chemistry of the ester reaction is a CO/H$_2$ mole ratio of 2:1 and of the ether reaction is 4:1. Mole ratios of CO/H$_2$ in the range from 6:1 to 1:2 can be employed in the ether reaction. Preferred ratios of CO/H$_2$ are in the range from 2.5:1 to 1.5:1 for the ester reaction and from 5:1 to 3:1 for the ether reaction. In the production of ethylidene diacetate, acetic anhydride is produced along with the ethylidene diacetate when less than the theoretical amount of hydrogen is employed, the ethylidene diacetate/acetic anhydride (EDA/Ac$_2$O) ratio varying as the amount of hydrogen varies. Methane make, resulting from the side reactions $$CH_3I + H_2 \rightarrow CH_4 + HI$$

$$CH_3CHO \rightarrow CH_4 + CO$$

increases with increasing hydrogen levels and under high hydrogen conditions, considerable H$_2$ consumption occurs so that its reactor partial pressure is drastically reduced.

The liquid reaction medium employed may include any solvent compatible with the catalyst system and may include ether or ester or mixtures of ether and ester feedstocks and/or the desired alkylidene diester. However, in accordance with the present process, the solvent system must include at least 9% carboxylic acid whose ester is to be produced. Once this minimum carboxylic acid concentration requirement is met, the actual amount of carboxylic acid employed can vary as desired although concentrations ranging from about 45% to about 65% have been found to be extremely efficacious. And as previously noted, if ethylidene diacetate is the desired diester product, the carboxylic acid employed will be acetic acid. Under such circumstances, the acetic acid may be obtained from any source, but it is convenient to use acetic acid which is coproduced in the process, one mole of acetic acid being made per mole of ethylidene diacetate produced. Additional acid may be added if necessary.

The process of the present invention is carried out under substantially anhydrous conditions. It is necessary, therefore, for suitable results to utilize ether and ester feedstocks as well as carbon monoxide and hydrogen streams that are essentially free of water. During start-up procedures for the process of the present invention, some residual water may be present in the reactor system. No substantial amounts of the alkylidene diesters will be produced until all the water has been removed from the reactor system or until all of the water has been consumed in the production of undesired by-product materials. Any conventional method for drying or dehydrating the feedstocks and reactants can be utilized to render them suitable for use in the process of the invention. As employed herein, the term "substantially anhydrous" means not more than 0.05 mole of water per mole of total ether or ester feed material present in the reactor.

The process of the present invention may be operated either as a batch or as a continuous process. In carrying out the present invention on a commercial scale, it is desirable to operate the process in a continuous mode. Such a continuous process can be very easily carried out in the liquid phase by preforming a liquid homogeneous phase that contains the rhodium component, the halogen component, the palladium cocatalyst, and the agent for generating carboxylic acid anions. For example, a rhodium component such as rhodium iodide and a palladium compound can be added to a small amount of an inert solvent or to a small amount of the reactant material such as dimethyl ether or to a small amount of the desired product such as ethylidene diacetate. The halogen component, such as methyl iodide, can also be added to this mixture as can the means for generating carboxylic acid anions and carbon monoxide can be thereafter bubbled through the liquid mixture to preform the liquid homogeneous phase that contains the components of the catalyst system. It is desirable to include a solvent material that has a boiling point above the boiling point of the diester product to contain the rhodium and palladium compounds and the halogen component. By using such a solvent component it is possible to separate the diester product from the reaction mixture without undesirable precipitation of the rhodium compound, the palladium compound, or the carboxylic acid anion-generating means from the reaction mixture. This preformed phase can then be added to the reactor along with at least one of the reactant materials such as methyl acetate. In most instances, it is desirable to also add an additional solvent to the reaction mixture.

The reactor used in the present invention can be constructed of any suitable corrosion-resistant material and can be equipped with a gas sparger below the surface of the liquid reaction mixture. The carbon monoxide-hydrogen gas mixture can be bubbled into the liquid reaction mixture continuously. The bubbling of the gas mixture through the liquid reaction mixture provides some degree of agitation but in most instances it will be desirable to mechanically agitate the reaction mixture with paddle wheels and the like to obtain the desired contact between the carbon monoxide and the liquid phase.

A small amount of the reaction mixture can be continuously withdrawn from the reactor and passed to a separation zone. The separation zone can be a conventional simple distillation column wherein the diester product such as ethylidene diacetate can be vaporized from the reaction mixture along with any unreacted feed materials such as the methyl acetate or dimethyl ether; or other volatile materials. The remaining liquid phase, containing the catalyst system components can then be recycled to the reactor. In some instances, it may also be desirable to utilize a flash tank for separating the diester product and the unreacted reactants from the reaction mixture. This can be conveniently accomplished by withdrawing a portion of the reaction mixture from the reactor and passing it to the tank maintained under reduced pressure either with or without the addition of heat, thus causing the diester product and the unreacted feed components and volatile materials to vaporize, leaving the rhodium and palladium compounds, the agent for liberation of carboxylic acid anions, and the halogen component (if nonvolatile) contained in the unvaporized liquid in the flash tank. This liquid in the flash tank can be recycled to the reactor. It is, of course, understood that the diester product can be further purified by conventional purification techniques that do not form a part of this invention.

It will be apparent to those skilled in the art that various modifications and changes may be made in the foregoing disclosure without departing from the spirit and scope of the invention.

The following examples are presented to illustrate embodiments of the invention. However, they should not be construed as limiting the invention in any manner whatsoever.

The term "selectivity" as employed in the following examples refers to molar selectivity and may be defined as the quotient of the moles of ethylidene diacetate (EDA) made during the course of the reaction, divided by the sum of the moles of EDA made plus the difference between the moles of acetic anhydride ($Ac_2O$) found in the reaction product and the moles of $Ac_2O$ input as a starting material. Expressed algebraically, % selectivity, then, is as follows:

$$\% \text{ Selectivity} = \frac{\text{moles EDA made}}{\text{moles Ac}_2\text{O made} + \text{moles EDA made}} \times 100$$

It will be noted that in those instances where acetic anhydride is consumed in the reaction, the term "moles $Ac_2O$ made" is considered to be zero, and percent selectivity to EDA is reported as 100%.

The term "yield" as employed in the following examples is on a molar basis and is the multiplication product of conversion times selectivity times 100. Algebraically, then, % yield is as follows:

$$\% \text{ Yield} = \text{conversion} \times \text{selectivity} \times 100$$

EXAMPLE 1

A 300-ml autoclave fitted into a system allowing constant pressure and temperature reactions in which pressure drop was measured from a higher pressure reservoir was employed as the reactor. The system was designed so that a liquid could be added to the pressure-sealed autoclave. Pressure in the reservoir, autoclave temperature and differential pressure were automatically recorded. The reservoir could be repressured during the reaction to allow for reactions requiring consumption of larger amounts of CO and hydrogen. The reactor was charged first with the weighed quantities of the solid materials, e.g., a rhodium salt and, where indicated, a palladium salt, then the liquid components in the desired amounts were added, i.e., the reactant methyl acetate, acetic acid and the promoter component where used. The autoclave was sealed and pressure-tested. At this point, when dimethyl ether was used as a reactant it was added to the autoclave through a valved side port under pressure (3.2 kg/cm$^2$) in the acetic acid solution from a pressure bottle.

The autoclave was then pressured to 4.5–8.1 kg/cm$^2$ with a mixture of CO and $H_2$ and heated to the reaction temperature. The methyl iodide promoter for the catalyst was then added from a liquid reservoir at 35.2–50.2 kg/cm$^2$ to initiate reaction. The autoclave was pressured to the desired level with the CO—$H_2$ mixture and the reaction allowed to proceed under stirring at a rate of 750 rpm for the desired reaction period. At the end of the reaction period, the reservoir was sealed from the autoclave and cooling was begun. At 25° C., the excess pressure was vented from the autoclave and the liquid product was analyzed by gas chromatography.

Using the above-described procedure, the reactor was charged with 0.001 mole $RhCl_3$-x $H_2O$, 0.313 mole methyl acetate (MeOAc), 1.203 mole acetic acid (AcOH), 0.0015 mole $PdCl_2$, and 0.006 mole triphenylphosphine [$(C_6H_5)_3P$]. The liquid reservoir contained 0.10 mole of methyl iodide (MeI). The concentration of acetic acid in the reaction medium was 64.7% by weight. The reaction was run for 6 hours at 174° C. using an analyzed CO/$H_2$ mixture (CO-65.8 mole %, $H_2$-34.1 mole %, $CO_2$-0.1 mole %) at a pressure of 35.2 kg/cm$^2$. Gas chromatographic analysis of the product showed:

|      | Mole % |
|------|--------|
| MeI  | 4.32   |
| MeOAc | 0.77  |
| AcOH | 88.60  |
| EDA  | 6.31   |

Calculations indicated that 96 mole % of the MeOAc had been converted to EDA, with no detectable $Ac_2O$ formation, giving a selectivity to EDA of 100% and a yield of 96%.

EXAMPLE 2-13

To show the criticality of the inclusion of the essential palladium cocatalyst according to the present invention in order to improve selectivity to EDA versus acetic anhydride in the carbonylation reaction, a series of experiments was performed using the reactor system of Example 1. In this series, the cocatalyst was omitted from the system, and then other metals of Group 8 of the Periodic Table of the Elements were substituted for the palladium cocatalyst. Although some of the Group 8 metals which were substituted for the essential palladium cocatalyst of the present invention have been known in the art to possess catalytic properties similar to palladium, the results shown in the following Table 1 show the unexpected criticality of the palladium cocatalyst in the catalyst system of this invention.

In each of the following runs (unless otherwise specified) the reactor was charged with 0.001 mole $RhCl_3$-x $H_2O$, 0.315 mole MeOAc, 1.20 mole AcOH, 0.012 mole $(C_6H_5)_3P$, and 0.0015 mole of $PdCl_2$ or the metal compound being substituted for the palladium cocatalyst. From the liquid reservoir in each case was added 0.100 mole MeI. In each run, a blend of 90% CO, 10% $H_2$ was employed. System pressure was 35.2 kg/cm$^2$ in each case, and system temperature was 175° C.

| EX. | COCATALYST | AcOH CONC. wt % | REACTION TIME, hrs. | SELECTIVITY TO EDA, Mole % |
|-----|------------|-----------------|---------------------|----------------------------|
| 2   | $PdCl_2$   | 63.6            | 2.5                 | 22.8                       |
| 2a[1] | $PdCl_2$ | 45.8            | 4.5                 | 21.8                       |
| 3   | None       | 63.8            | 15.8                | 10.1                       |
| 4   | $PtCl_2$   | 63.6            | 4.7                 | 10.7                       |
| 5   | $RuCl_3$   | 63.6            | 3.8                 | 9.0                        |
| 6   | $IrCl_3$   | 63.5            | "                   | 10.1                       |
| 7   | $RhCl_3$ (excess) | 63.6     | 4.2                 | 11.5                       |
| 8[2] | $FeCl_3$  | 63.6            | 3.5                 | 10.5                       |
| 9   | $CoCl_2$   | 63.7            | 4.0                 | 10.2                       |
| 10  | $NiCl_2$   | 63.7            | 5.7                 | 9.3                        |
| 10a | $NiCl_2$   | 63.7            | 1.1                 | 11.7                       |
| 11  | $H_2PtCl_6.6H_2O$ | 63.3     | 4.0                 | 10.0                       |
| 12  | $H_2OsCl_6.2H_2O$ | 63.4     | 4.0                 | 10.5                       |
| 13  | $ReCl_3$   | 63.5            | 3.5                 | 9.9                        |

[1] AcOH (0.867 mole) and $Ac_2O$ (0.20 mole) was employed.
[2] A heavy white precipitate appeared in the reactor which may have lowered the reported 10.5% selectivity to EDA.

As can be seen from the results in the Table, even though at the lower end of the hydrogen concentration range (10 mole %), the selectivity to EDA in general tends to be relatively low, only the palladium cocatalyst provided a significant improvement over the system of Example 3 which contained no cocatalyst. This result is quite surprising in view of the recognition in the art that metals such as nickel, cobalt, iron, platinum and ruthenium are quite similar to palladium in catalyzing reactions such as, e.g., hydrogenation reactions.

EXAMPLE 14

Using the reactor system described in Example 1, the following example was run to show the effect of lithium acetate (LiOAc) as the agent for liberation of acetate ions in lieu of the triphenylphosphine used in Example 1.

The reactor was charged with 0.001 mole $RhCl_3$-x $H_2O$, 0.938 mole MeOAc, 0.164 mole AcOH, 0.100 mole $Ac_2O$, 0.0015 mole $PdCl_2$, and 0.010 mole LiOAc. The liquid reservoir contained 0.10 mole of MeI. The concentration of acetic acid in the reaction medium was 9.4%. Temperature, pressure and $CO/H_2$ ratio were as in Example 1. Analysis of the reaction products showed 99.2% selectivity to EDA with 74.7% conversion of MeOAc, resulting in a 74.1% yield.

EXAMPLES 15-19

To show the effect of omitting one or more components of the reaction system of the invention, a series of runs was made using the reactor described in Example 1. Temperature, pressure, and $CO/H_2$ ratio were as in Example 1. The results are shown in the following Table 2.

As can be seen from the results shown in the Table, deletion of one or more of the necessary components according to the invention, (i.e., the palladium catalyst, the acetic acid, and the promoter component) results in a decrease in either the selectivity of the reaction to EDA or the conversion of the ester charge stock or both.

TABLE 2

| EX. | $RhCl_3$—x $H_2O$ moles | $PdCl_2$ moles | MeI moles | LiOAc moles | $(C_6H_5)_3P$ moles | MeOAc moles | AcOH moles | AcOH wt % | $Ac_2O$ moles | Reaction Time hrs. |
|---|---|---|---|---|---|---|---|---|---|---|
| 15 | 0.0010 | 0 | 0.100 | 0.010 | 0.006 | 0.315 | 1.20 | 64.3 | 0 | 3.5 |
| 16 | 0.0010 | 0.0015 | 0.100 | 0.010 | 0 | 0.938 | 0 | 0.0 | 0.20 | 7.0 |
| 17 | 0.0010 | 0.0015 | 0.100 | 0 | 0 | 0.938 | 0.164 | 9.4 | 0.10 | 7.0 |
| 18 | 0.0010 | 0 | 0.100 | 0 | 0.006 | 0.315 | 1.20 | 64.7 | 0 | 3.5 |
| 19 | 0.0010 | 0.0015 | 0.100 | 0 | 0 | 0.315 | 1.20 | 65.4 | 0 | 3.0 |

| Example | Conversion MeOAc (Mole %) | Selectivity to EDA (Mole %) | Yield EDA (Mole %) |
|---|---|---|---|
| 15 | 91.5 | 60.5 | 55.3 |
| 16 | 52.6 | 100.0 | 52.6 |
| 17 | 31.8 | 100.0 | 31.8 |
| 18 | 97.2 | 77.0 | 74.8 |
| 19 | 64.7 | 51.7 | 33.4 |

EXAPMLE 20

To illustrate the carbonylation of an ether feedstock according to the present invention, the following experiment was performed using the reactor of Example 1.

Using the procedure of Example 1, the reactor was charged with 0.001 mole $RhCl_3$-x $H_2O$, 0.309 mole dimethyl ether ($Me_2O$), 0.978 mole acetic acid (AcOH), 0.190 mole acetic anhydride, 0.0015 mole $PdCl_2$, and 0.010 mole lithium acetate. The liquid reservoir contained 0.10 mole of methyl iodide (MeI). The concentration of acetic acid in the reaction medium was 54.5%. The reaction was run for 6 hours at 175° C. using an analyzed $CO/H_2$ mixture (CO-79 mole %, $H_2$-21 mole %) at a pressure of 42.2 kg/cm² Gas chromatographic analysis of the product showed 100% selectivity of reaction of the dimethyl ether to EDA, with greater than 99% conversion of the ether.

EXAMPLES 21-30

Several reactions were run using a catalyst comprising 0.0010 mole $RhCl_3$-x $H_2O$ and 0.10 mole MeI. The reactions, with $PdCl_2$ as cocatalyst, were conducted at temperatures from 160° C. to 175° C. and pressures from 35.2 kg/cm² to 49.2 kg/cm² over reaction periods varying from 3 hours to 6 hours. Reaction conditions and results are shown in Table 3.

TABLE 3

| EX. | $RhCl_3$—x $H_2O$ moles | $PdCl_2$ moles | MeI moles | LiOAc moles | $(C_6H_5)_3P$ moles | MeOAc moles | AcOH moles | AcOH wt % | $Ac_2O$ moles | $CO/H_2$ Moles % | PRESSURE kg/cm² | TEMP. °C. | REACTION TIME hrs. |
|---|---|---|---|---|---|---|---|---|---|---|---|---|---|
| 21 | 0.0010 | 0.0015 | 0.10 | 0.010 | 0 | 0.938 | 0.172 | 9.8 | 0.095 | 66/34 | 35.2 | 175 | 6.0 |
| 22 | 0.0010 | 0.0015 | 0.10 | 0 | 0.0025 | 0.938 | 0.172 | 9.8 | 0.095 | 66/34 | 35.2 | 175 | 6.0 |
| 23 | 0.0010 | 0.0015 | 0.10 | 0.010 | 0.0025 | 0.938 | 0.172 | 9.8 | 0.095 | 66/34 | 35.2 | 175 | 6.0 |
| 24 | 0.0010 | 0.0015 | 0.10 | 0 | 0.012 | 0.315 | 1.20 | 63.6 | 0 | 90/10 | 35.2 | 175 | 6.0 |
| 25 | 0.0010 | 0.0015 | 0.10 | 0.010 | 0 | 0.315 | 1.20 | 65.1 | 0 | 66/34 | 35.2 | 175 | 6.0 |
| 26 | 0.0010 | 0.0015 | 0.10 | 0.010 | 0.0060 | 0.315 | 1.20 | 64.1 | 0 | 66/34 | 35.2 | 175 | 6.0 |
| 27 | 0.0010 | 0.0015 | 0.10 | 0.010 | 0.0060 | 0.313 | 1.20 | 64.2 | 0 | 66/34 | 35.2 | 160 | 3.0 |
| 28 | 0.0010 | 0.0015 | 0.10 | 0.010 | 0.0060 | 0.313 | 1.20 | 64.2 | 0 | 66/34 | 35.2 | 175 | 3.0 |
| 29 | 0.0010 | 0.0015 | 0.10 | 0.010 | 0.0060 | 0.313 | 1.20 | 64.2 | 0 | 66/34 | 21.1 | 175 | 3.0 |
| 30 | 0.0010 | 0.0015 | 0.10 | 0.010 | 0.0060 | 0.313 | 1.20 | 64.2 | 0 | 66/34 | 49.2 | 175 | 3.0 |

| Example | Conversion MeOAc (Mole %) | Selectivity to EDA (Mole %) | Yield EDA (Mole %) |
|---|---|---|---|
| 21 | 53.0 | 83.0 | 44.0 |
| 22 | 66.0 | 68.5 | 45.2 |
| 23 | 86.0 | 55.6 | 47.8 |
| 24 | 100.0 | 22.8 | 22.8 |
| 25 | 97.0 | 87.8 | 85.2 |
| 26 | 98.0 | 100.0 | 98.0 |
| 27 | 87.9 | 77.9 | 68.5 |
| 28 | 78.2 | 94.6 | 74.0 |
| 29 | 83.7 | 79.0 | 66.1 |

TABLE 3-continued

| | 30 | 96.7 | 100.0 | 96.7 |
|---|---|---|---|---|

What is claimed is:

1. A process for the production of alkylidene diesters which comprises contacting a reactant selected from the group consisting of ethers having the formula R—O—R' and esters having the formula $$R-\overset{O}{\underset{\|}{C}}-O-R'$$

wherein R and R' are saturated aliphatic hydrocarbon groups containing from 1 to 5 carbon atoms each and mixtures of said compounds with carbon monoxide, hydrogen and a catalyst system consisting essentially of a rhodium compound, a halogen component selected from the group consisting of bromine, iodine, bromides and iodides, a cocatalyst palladium compound, and promoter means for liberation of anions of the carboxylic acid whose ester is to be produced selected from the group consisting of tertiary phosphines, tertiary arsines, tertiary stibines, tertiary amines, the lithium salt of the carboxylic acid, and mixtures thereof, said contacting being effected in the liquid phase in a solvent comprising at least 9% of the carboxylic acid whose ester is to be produced under substantially anhydrous conditions at a temperature within the range from about 150° to about 190° C., at a carbon monoxide partial pressure in the range from 1 to 1100 kg/cm$^2$ and with an amount of hydrogen from about 5 to about 40 mole percent of the carbon monoxide/hydrogen mixture.

2. The process of claim 1 wherein the amount of said palladium compound is in the range of about 0.1 to about 10 moles per mole of the rhodium compound in said catalyst system.

3. The process of claim 1 wherein the reaction promoter is present in amounts from 1000:1 to about 1:1 times the molar amount of rhodium component.

4. The process of claim 3 wherein said reactant is an ester, one mole of carbon monoxide is employed per mole of ester and the amount of hydrogen employed is from about 20 to about 40 mole percent of the carbon monoxide/hydrogen mixture.

5. The process of claim 4 wherein said rhodium compound of said catalyst system is selected from the group consisting of rhodium salts, rhodium oxides and rhodium carbonyl complexes.

6. The process of claim 5 wherein said halogen component is an iodide.

7. The process of claim 6 wherein said ester is methyl acetate, said rhodium compound is selected from rhodium trichloride, rhodium triiodide, and dirhodium tetracarbonyl diiodide, said iodide is methyl iodide, said cocatalyst is palladium chloride, said reaction promoter is triphenylphosphine, and said acid is acetic acid.

8. The process of claim 6 wherein said ester is methyl acetate, said rhodium compound is selected from rhodium trichloride, rhodium triiodide, and dirhodium tetracarbonyl diiodide, said iodide is methyl iodide, said cocatalyst is palladium chloride, said reaction promoter is lithium acetate, and said acid is acetic acid.

9. The process of claim 6 wherein said ester is methyl acetate, said rhodium compound is selected from rhodium trichloride, rhodium triiodide, and dirhodium tetracarbonyl diiodide, said iodide is methyl iodide, said cocatalyst is palladium chloride, said reaction promoter is a mixture of triphenylphosphine and lithium acetate, and said acid is acetic acid.

10. The process of claim 3 wherein said reactant is an ether, two moles of carbon monoxide are employed per mole of ether and the amount of hydrogen employed is from about 15 to about 30 mole percent of the carbon monoxide/hydrogen mixture.

11. The process of claim 10 wherein said rhodium compound of said catalyst system is selected from the group consisting of rhodium salts, rhodium oxides and rhodium carbonyl complexes.

12. The process of claim 11 wherein said halogen component is an iodide.

13. The process of claim 12 wherein said ether is dimethyl ether, said rhodium compound is selected from rhodium trichloride, rhodium triiodide, and dirhodium tetracarbonyl diiodide, said iodide is methyl iodide, said cocatalyst is palladium chloride, said reaction promoter is triphenylphosphine, and said acid is acetic acid.

14. The process of claim 12 wherein said ether is dimethyl ether, said rhodium compound is selected from rhodium trichloride, rhodium triiodide, and dirhodium tetracarbonyl diiodide, said iodide is methyl iodide, said cocatalyst is palladium chloride, said reaction promoter is lithium acetate, and said acid is acetic acid.

15. The process of claim 12 wherein said ether is dimethyl ether, said rhodium compound is selected from rhodium trichloride, rhodium triiodide, and dirhodium tetracarbonyl diiodide, said iodide is methyl iodide, said cocatalyst is palladium chloride, said reaction promoter is a mixture of triphenylphosphine and lithium acetate, and said acid is acetic acid.

16. The process of claim 1 wherein the solvent comprises 45% to 65% of the carboxylic acid whose ester is to be produced.

17. The process of claim 16 wherein the carboxylic acid is acetic acid and the ester to be produced is ethylidene diacetate.

18. A process for the production of ethylidene diacetate which comprises contacting a reactant selected from the group consisting of dimethyl ether and methyl acetate and mixtures of said compounds with carbon monoxide, hydrogen and a catalyst system consisting essentially of a rhodium compound, a halogen component selected from the group consisting of bromine, iodine, bromides and iodides, a cocatalyst palladium compound, and promoter means for liberation of anions of acetic acid selected from the group consisting of tertiary phosphines, tertiary arsines, tertiary stibines, tertiary amines, the lithium salt of acetic acid, and mixtures thereof, said contacting being effected in the liquid phase in a solvent comprising at least 9% of acetic acid under substantially anhydrous conditions at a temperature within the range from about 150° to about 190° C., at a carbon monoxide partial pressure in the range from 1 to 1100 kg/cm$^2$ and with an amount of hydrogen from about 5 to about 40 mole percent of the carbon monoxide/hydrogen mixture.

19. A process for the production of ethylidene diacetate which comprises contacting a reactant selected from the group consisting of dimethyl ether and methyl acetate and mixtures of said compounds with carbon monoxide, hydrogen and a catalyst system consisting essentially of a rhodium compound, a halogen component selected from the group consisting of bromine, iodine, bromides and iodides, a cocatalyst palladium compound, and promoter means for liberation of anions of acetic acid selected from the group consisting of tertiary phosphines, tertiary arsines, tertiary stibines, tertiary amines, the lithium salt of acetic acid, and mixtures thereof, said contacting being effected in the liquid phase in a solvent comprising from about 9% to about 65% of acetic acid under substantially anhydrous conditions at a temperature within the range from about 150° to about 190° C., at a carbon monoxide partial pressure in the range from 1 to 1100 kg/cm$^2$ and with an amount of hydrogen from about 10 to about 40 mole percent of the carbon monoxide/hydrogen mixture.

20. The process of claim 19 wherein the solvent comprises 45% to 65% of acetic acid, and the amount of hydrogen employed is from about 15 to about 40 mole percent of the carbon monoxide/hydrogen mixture.

* * * * *

UNITED STATES PATENT AND TRADEMARK OFFICE
CERTIFICATE OF CORRECTION

PATENT NO. : 4,810,821
DATED : March 7, 1989
INVENTOR(S) : Frank E. Paulik et al It is certified that error appears in the above-identified patent and that said Letters Patent is hereby corrected as shown below:

In column 6, line 36, delete "255" and insert therefor --225--.

In column 12, line 21, delete "EXAPMLE" and insert therefor --EXAMPLE--.

Signed and Sealed this

Sixth Day of February, 1990

Attest:

JEFFREY M. SAMUELS

*Attesting Officer*  *Acting Commissioner of Patents and Trademarks*